(12) United States Patent
Burstyn et al.

(10) Patent No.: US 7,105,274 B2
(45) Date of Patent: Sep. 12, 2006

(54) PHOTOLUMINESCENT ETHYLENE SENSORS

(75) Inventors: Judith N. Burstyn, Madison, WI (US); Arthur B. Ellis, Falls Church, VA (US); Omar Green, Madison, WI (US); Nickolaus A. Smith, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/859,484

(22) Filed: Jun. 2, 2004

(65) Prior Publication Data
US 2005/0031985 A1    Feb. 10, 2005

Related U.S. Application Data (60) Provisional application No. 60/475,103, filed on Jun. 2, 2004.

(51) Int. Cl.
G03F 7/004    (2006.01)

(52) U.S. Cl. .................................... 430/270.1
(58) Field of Classification Search ............. 430/270.1
See application file for complete search history.

(56) References Cited

U.S. PATENT DOCUMENTS

| | | | |
|---|---|---|---|
| 4,861,727 A | 8/1989 | Hauenstein et al. | |
| 5,190,729 A | 3/1993 | Hauenstein et al. | |
| 5,425,869 A * | 6/1995 | Noding et al. | 204/418 |
| 6,399,224 B1 | 6/2002 | Li | |
| 6,558,626 B1 | 5/2003 | Aker et al. | |
| 2001/0013273 A1 | 8/2001 | Kang et al. | |
| 2001/0015334 A1 | 8/2001 | Kang et al. | |
| 2002/0076822 A1 * | 6/2002 | Levitsky et al. | 436/104 |
| 2002/0162456 A1 | 11/2002 | Kang et al. | |
| 2003/0023181 A1 | 1/2003 | Mault | |
| 2003/0134959 A1 | 7/2003 | Hancock et al. | |
| 2003/0228701 A1 * | 12/2003 | Wong et al. | 436/126 |
| 2004/0124336 A1 * | 7/2004 | MacCraith et al. | 250/208.2 |

FOREIGN PATENT DOCUMENTS

| | | |
|---|---|---|
| WO | WO 00/23791 | 4/2000 |
| WO | WO 2003/048226 | 6/2003 |

OTHER PUBLICATIONS

Green, O., et al., "AgBF4-Impregnated Poly(vinyl phenyl ketone): An Ethylene Sensing Film," Abstract and Supporting Information.
Green, O., et al., "Coinage-Metal-Based Luminescent Ethylene Sensors," Jun. 2-4, 2002 34th Great Lakes Regional Meeting of the American Chemical Society Abstract.
Green, O., et al., "Coinage-metal-Based Luminscent Ethylene Sensors," Aug. 18, 2002-Aug. 22, 2002 Poster Presentation at National ACS Meeting in Boston, MA.

(Continued)

Primary Examiner—Amanda Walke
(74) Attorney, Agent, or Firm—Quarles & Brady LLP (57) ABSTRACT

A photoluminescent polymer/transition metal complex is disclosed which is capable of selectively binding to alkenes to thereby alter the photoluminescence of the complex. In one embodiment, a poly(vinyl phenyl ketone)/Ag(I) complex is disclosed which reversibly and selectively binds with ethylene. The disclosed photoluminescent polymer/transition metal complex can be used as part of a sensor to determine the presence and/or concentration of alkenes such as ethylene.

20 Claims, 8 Drawing Sheets

OTHER PUBLICATIONS

Heeger, P.S. et al., "Making sense of polymer-based biosensors," PNAS 96:12219-12221 (1999).

Kim, H.S., et al., "Reversible olefin complexation by silver ions in dry poly(vinyl methyl ketone) membrane and its application to olefin/paraffin separations," Chem. Commun. 2000 1261-1262.

Liu, W., et al., "Lanthanide Coordination Polymers and Their Ag+-Modulated Fluorescence," J. Am. Chem. Soc. 2004 126:2280-2281.

Miller, M. T., et al., "Oxygen sensing by photoluminescnce quenching of a heteroleptic copper (l) bis(phenanthroline) complex immobilized in polystyrene," 1999 61:222-224.

Wang, D., et al., "Biosensors from conjugated polyelectrolyte complexes," PNAS 2002 99:49-53.

Lakowicz, Joseph R., Principles of Fluorescene Spectroscopy, 2nd ed., Kluwer Academic/Plenum Publishers, NY, p. 531 (1999).

* cited by examiner

FIG 6 poly (vinyl phenyl ketone) PVPK poly (vinyl p-methoxyphenyl ketone)

poly (vinyl p-phenylphenyl ketone)

PHOTOLUMINESCENT ETHYLENE SENSORS

CROSS-REFERENCE TO RELATED APPLICATIONS

This application claims the benefit of U.S. Provisional Patent Application No. 60/475,103, filed Jun. 2, 2003, incorporated by reference as if set forth herein in its entirety.

STATEMENT REGARDING FEDERALLY SPONSORED RESEARCH OR DEVELOPMENT

This invention was made with United States government support under NIH grant number HL65217. The United States has certain rights in this invention.

BACKGROUND OF THE INVENTION

The present invention relates to a solid solution that comprises a complex between a photoluminescent polymer and a transition metal capable of binding to an alkene. Such a solid solution can be employed as a sensor for monitoring the level of at least one gaseous alkene (also known as an 'olefin'). The invention finds particular utility in monitoring gaseous ethylene during shipment and storage of fresh produce. A robust market exists for the sale of ethylene detection and ethylene removal products, but these products have various shortcomings, noted below. New strategies for sensing ethylene at commercially relevant levels are essential to development of cost-effective monitoring devices.

Three environmental factors—temperature, humidity and ethylene concentration—influence the development and ripening of fresh produce. Control over these three factors is essential for efficient produce transport, storage and induced ripening. Temperature and humidity are easily and precisely controlled, while ethylene concentration is more difficult to control. It is commercially important to avoid premature exposure of fruits, vegetables, flowers and other plant products to ethylene because exposure to as little as 10 ppb ethylene initiates ripening. Moreover, while short-term exposure to high ethylene concentrations (1000–100,000 ppb) is required to induce rapid ripening, prolonged exposure inevitably leads to premature rotting and attendant financial losses. On the other hand, timely exposure of unripe fruit to ethylene at a suitable level desirably induces ripening.

Commercial fruit and vegetable growers harvest products in a slightly immature state to facilitate processing and transport, and store the unripe fruit in carefully controlled environments until ripening is desired. To initiate ripening, produce is processed to ensure that the product reaches market in an optimal state. Each product type requires specific conditions, including a specific ethylene concentration range and duration of exposure, for optimal market quality. Suitable ethylene control involves both (1) monitoring ethylene gas concentration over a range of between about 10 and 100,000 ppb and (2) adjusting the concentration as needed.

Ethylene is typically measured by metal oxide resistivity, by chemiluminescence on reaction with ozone, or by gas chromatography. Each method has drawbacks. Metal oxide sensors can be inaccurate as they are susceptible to interference from other analytes, from flow rate variations and from ambient oxygen. Chemiluminescence systems require ozone generation and are therefore expensive and potentially dangerous. Gas chromatography is accurate and specific but the instrumentation is costly and the method is not well-suited to real time sensing. Moreover, existing ethylene sensors are not ideal for routine use because they lack sufficient sensitivity and they are prohibitively expensive. Available commercial sensors cannot function below 200 ppb ethylene, notwithstanding the botanically-relevant 10 ppb level. The $1,000–$13,000 cost per unit also precludes widespread use of these devices.

Likewise, existing ethylene removal strategies are hampered by expense and by the shortcomings in available sensors. Existing removal strategies include simple adsorption and oxidation by supported permanganate. A catalytic oxidation device, the Bio-KES 348 Ethylene Removal System, can maintain ethylene levels as low as 10 ppb; but requires continuous UV irradiation and consumes 475 Watts. If this device were coupled to a low cost, accurate sensor/actuator system, it could be operated cost effectively in ripening chambers.

Some metals are well known to interact strongly with alkenes under some conditions, and are therefore a reasonable choice for sensor handles. There is precedent for the use of, e.g., coinage metals in ethylene sensing, as plants use copper in their ethylene receptor proteins and silver is used both to inhibit the ethylene response in cut flowers and to extract alkenes from petrochemical feedstreams. The chemistry of coinage metals provides fertile ground for the design of new ethylene sensor technology.

Coinage metals are used to separate gaseous alkenes and alkanes (also called 'paraffins') in the petrochemical industry. In solution separations, silver(I) or copper(I) salts are dissolved in a stabilizing solvent, thereby promoting metal-alkene interaction while inhibiting decomposition of the active metal ions. When crude gas streams are passed through the solution, alkenes bind to metal ions therein, and an alkene-enriched solution is collected. The alkenes are released from solution by heating, to produce a high purity alkene gas mixture.

Figure 1:
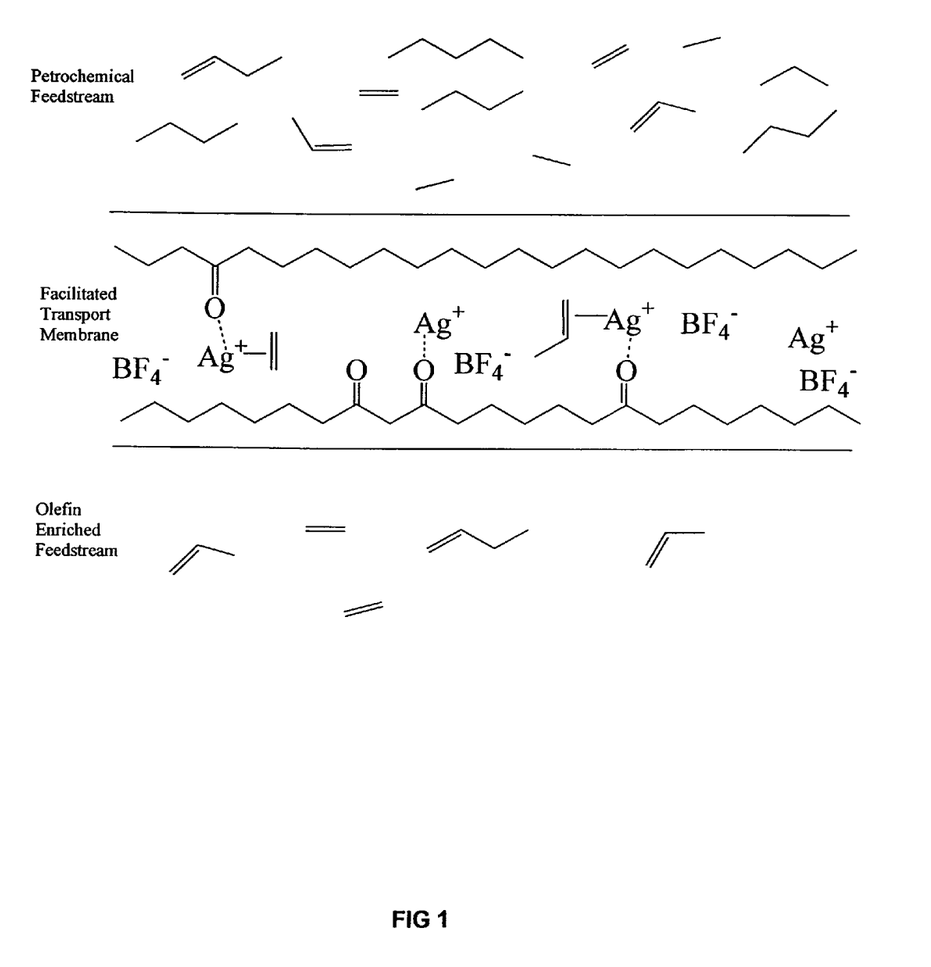
FIG. 1 depicts facilitated transport occurring when alkenes bind to $Ag^+$ ions, diffusing from ion to ion through a membrane.

Gaseous alkenes and alkanes are also separated from input gas streams by differential membrane permeability in facilitated transport processes wherein silver(I) or copper(I) salts are suspended in a polymer membrane that acts both as a support and as a metal ion ligand. The metal ions preferentially bind alkenes from the input gas stream, and the alkenes pass through the membrane by rapid diffusion from one metal center to another. The metal ions selectively facilitate the passage of alkenes through the membrane, thereby generating a purified alkene gas stream. A schematic diagram of facilitated transport is shown in FIG. 1. Facilitated transport is distinguished from the present invention in that it does not involve luminescence or sensing, and cannot because the polymers there employed lack the extended conjugation structures employed in the present invention.

Silver(I) salts are highly effective in facilitated transport applications because membranes impregnated with Ag(I) salts are stable and bind alkenes strongly but reversibly. Bound alkenes are readily removed from the membranes by mild desorption methods such as heating. Cu(I) can also be used in facilitated transport processes, but care must be taken to minimize disproportionation of the Cu(I) ion. Since disproportionation is bimolecular, Cu(I)-impregnated polymers are stable only if the polymer separates the metal centers effectively.

A key criterion for an effective transport polymer appears to be that the polymer bears a functional group capable of interacting with the metal centers. Polyoxazoline, cellulose acetate, polypyrrolidinone and polyethyleneoxide polymers can effectively separate alkenes and alkanes in commercial facilitated transport membranes. Many of these polymers contain electronegative oxygen atoms to bind the metal ions. Also, interaction between silver(I) ions and the oxygen atoms promotes the alkene-Ag(I) interaction. Ethylene transport by poly(vinyl methyl ketone) (PVMK) has been studied in some detail, revealing the molecular interactions that occur in this process. Silver ions interact directly with the carbonyl groups in PVMK, decreasing the frequency of the carbonyl vibrations. When ethylene binds to the silver ions, the carbonyl vibrational frequency increases slightly, suggesting that both the carbonyl and the alkene are within the coordination sphere of the metal. The fact that spectral changes are observed demonstrates that the polymer responds to the presence of the alkene. Nevertheless, there has been no suggestion to employ such polymers in a sensor system.

The efficacy of facilitated transport membranes depends on easy access of the alkene to the metal centers in the polymer matrix. A primary determinant of access to the metal ion is the strength of interaction between the metal cation and the counter-anion. Considerable improvement in the rate of alkene transport is achievable by varying the counter-ion. Because ethylene binding to closed shell $Ag^+$ and $Cu^+$ ions is calculated to involve both covalent and electrostatic components, soft electron-rich counter-ions compete with alkenes more effectively than hard electron-poor ions.

Counter-ion size and polarizability are both important to matrix structure. Large bulky counter-ions cannot approach the metal ion closely, thereby decreasing the strength of the electrostatic attraction. At the same time, small alkene molecules can enter spaces created in the polymer matrix by such large counter-ions. In 1-hexene:Ag(I) complexes with $CF_3CO_2^-$, $BF_4^-$, $NO_3^-$, and $CF_3SO3^-$ counter-ions, the metal-alkene bond strength correlates more strongly with the size of the counter-ion than with its basicity. On the other hand, the donor ability of the ion is also a matrix structure determinant. For example, poly(2-ethyl-2-oxazoline) impregnated with $AgBF_4$ gives rise to a more porous polymer matrix and to substantially more rapid passage of alkene than the same polymer impregnated with $AgClO_4$. In the aforementioned system, the silver ions are three-coordinate in the presence of the electron poor $BF_4^-$ anion and four-coordinate in the presence of $ClO_4^-$, an observation that is more reasonably explained by donor ability than by size. Interestingly, there has been little effort to apply many of the very large, weakly interacting counter-anions commonly used in inorganic synthesis to facilitated transport systems.

SUMMARY OF THE INVENTION

The present invention satisfies the need for improved ethylene sensing technology for use by producers, shippers, and warehousers of fruits, vegetables, flowers and other produce. It is here disclosed that ethylene induces photoluminescence changes in a solid solution that comprises a transition metal capable of binding an alkene and a photoluminescent polymer having functional moieties that interact with the transition metal. It is further disclosed that these solid solutions can serve as the basis for a commercially useful alkene sensor. Photoluminescence by the polymer can be observed after exposing the solid solution to light at an emission-inducing wavelength. Photoluminescence detection is an ideal design vehicle for new sensor devices, as the detection scheme can offer sensitivity to the parts per trillion level and employs only simple instrumentation.

Polymers for use in the invention must complex with a transition metal to allow the reversible interaction of transition metal ions and alkenes. The polymers must also solvate salts of the transition metal, by allowing separation between the metal cation and the anion of the metal salt. The polymer must also have electronic conjugation that allows luminescence, possibly by, but not limited to $n \rightarrow \pi^*$ or $\pi \rightarrow \pi^*$ transitions. Further, suitable polymers in a solid solution according to the invention respond to ethylene exposure with an observable change in luminescence intensity or wavelength.

A polymer can be rendered luminescent, or the luminescence can be altered, by adjusting the aromaticity of, or by extending conjugation of, its functional groups. Suitable classes of polymer include: polymers with carbonyl and aromatic functional groups, including but not limited to poly(vinyl phenyl ketone) (PVPK), polymers with aromatic groups only (including but not limited to polystyrene), polymers with carbonyl and heteroatom-containing aromatic functional groups (including but not limited to 5-pyridyl vinyl ketone), polymers with heteroatom-containing aromatic groups only (including but not limited to polyvinyl pyridine). The polymer can have a backbone that is saturated or unsaturated; for example, a polyethylene backbone can be suitable. The polymer backbone can contain unsaturated moieties, including rings or multiple bonds, and the unsaturated sites can be isolated or in conjugation. The polymer backbone can include conjugated or isolated, substituted or unsubstituted phenyl rings, double bonds or triple bonds. A particularly useful polymer has conjugated acetophenone (1-phenyl-ethanone) groups attached to an unconjugated backbone, i.e. PVPK. Other suitable polymers include, but are not limited to, poly(p-phenylene vinylene) (PPV), poly (vinyl p-methoxy phenyl ketone), and poly(vinyl p-phenyl phenyl ketone). The backbone or side chains within the polymer can be further derivatized at any available carbon to improve solubility, enhance conjugation or to shift absorption or emission wavelengths. For example, PVPK can be modified by addition of an electron donating methoxy group or a conjugated phenyl ring in the para phenyl position, causing an advantageous change in optical properties. Appended R groups can be selected to increase polymer solubility, improve optical properties, or provide additional functional interaction with the metal, or any combination of the above. Luminescent inorganic polymers can also be employed in the invention; for example lanthanide coordination polymers (e.g. europium) as in Liu, W., et al., "Lanthanide Coordination Polymers and Their $Ag^+$-Modulated Fluorescence," J. Am. Chem. Soc. 126:2280–2281 (2004), incorporated by reference as if set forth herein in its entirety. The polymer size is selected for processibility in that the polymer must be capable of being solubilized so that the metal salt can be introduced; when the solvent is removed a solid solution comprising the polymer, the metal cations and anions results. A polymer molecular weight of approximately 2500 g/mol is suitable for PVPK and its derivatives.

In still another aspect, the metal is preferably provided in the solid solution as a metal salt, in a specific molar ratio relative to the polymer functional groups. Appropriate ratios for each polymer/metal solution can be empirically determined by routine experimentation. When selecting suitable molar ratios of the polymer and metal salt in the solution, it is believed to be important to provide the metal in a coordinatively unsaturated state, such that polymer emission can undergo a reversible change in luminescence that varies in proportion to ethylene concentration, although the applicant does not intend to be bound by a particular theory of the invention. The metal ion participates in the function of the sensor, in that it is in electronic communication with the conjugated photoluminescent portion of the polymer and, as a result, transduces a signal to the polymer upon olefin binding. The metal is not provided merely to enhance polymer luminescence, but rather as an integral component of a sensing locus that comprises the extended conjugated moiety of the luminescent polymer and the metal itself. In the absence of the metal, the sensor of the invention cannot function. The performance of metal ions in the invention is determined by the degree of complexation with alkenes, which is in part determined by electronegativity. Electronegativity refers to a measure of attraction for shared electrons when one atom binds to other atoms. The electronegativity values of selected metals are shown in Table 1 below.

TABLE 1

Electronegativity of Transition Metals

| Transition Metals | Sc | Ti | V | Cr | Mn | Fe | Co | Ni | Cu |
|---|---|---|---|---|---|---|---|---|---|
| Electronegativity | 1.4 | 1.5 | 1.6 | 1.7 | 1.6 | 1.8 | 1.9 | 1.9 | 1.9 |
| Transition Metals | Y | Zr | Nb | Mo | Tc | Ru | Rh | Pd | Ag |
| Electronegativity | 1.3 | 1.3 | 1.6 | 2.2 | 1.9 | 2.2 | 2.3 | 2.2 | 1.9 |
| Transition Metals | La | Hf | Ta | W | Re | Os | Ir | Pt | Au |
| Electronegativity | 1.0 | 1.3 | 1.5 | 2.4 | 1.9 | 2.2 | 2.2 | 2.3 | 2.5 |

If the electronegativity of a metal is high, a metal atom will more strongly attract electrons when it binds with other atoms. If the electronegativity of a metal is too high, the possibility of irreversible reaction between metals and alkenes become large, and thus, the metal is not suitable as a sensor component. On the other hand, however, if the electronegativity of a metal is too low, it cannot function in the invention because of the low interaction with alkenes.

Therefore, the electronegativity of a metal used in the invention is preferable when in the range of about 1.6 to 2.3 in order that transition metal ions react reversibly with alkenes. Preferred transition metals within the above ranges include Mn, Fe, Co, Ni, Cu, Mo, Ru, Rh, Pd, Ag, Re, Os, Ir, Pt, or a complex thereof and so on. The Group VIII metals are also believed to be useful in the method.

The anions of the transition metal salts play an important role in the sensing event, as they modulate the reactivity of the metal cations with alkenes. Suitable anions must form ion pairs of moderate strength with the metal ion; strong ion pairing inhibits alkene binding but excessively weak ion pairing may compromise the reversibility of alkene interaction. For the polymer-metal ion complex to serve as an effective sensor, the metal salt must be solvated within the polymer, with functional groups on the polymer stabilizing the metal cation, promoting ion pair separation, as shown in Scheme 1 below. An alkene, such as ethylene, forms a specific, reversible interaction with the metal ion. The strength of this interaction is modulated by the anion according the relative thermodynamic properties of the ion pair and ethylene-metal interactions, according to the second equilibrium step in Scheme 1 below.

[Scheme 1] MX is the metal salt, [P] is a functional group of the polymer and A is the alkene. Both the polymer functional group and the alkene form specific interactions with the metal ion. The reversibility of this interaction is a function of the equilibrium in step 2. In the present invention, P is a luminescent polymer and the binding of the alkene to the metal ion alters the luminescent properties of the polymer.

The tendency of the polymer to solvate the metal salts arises from the functional groups present in the polymer, and the dielectric constant of the polymer. Ion pair separation is promoted by the presence of functional groups, such as a carbonyl group, other heteroatom or aromatic ring, which bind specifically to the metal cations, or by high dielectric constants that promote separation of the metal cation-anion pair. Solvation of the anion, through hydrophobic or donor-acceptor interactions is also important. Anion characteristics that promote ion pair separation include, but are not limited to, large bulky anions, anions with hydrophobic or aromatic functional groups, and anions with highly electronegative substituents.

Anions of the metal salt are preferably selected from those for which the metal salt has low lattice energy, to facilitate charge separation, and with hydrophobic or highly electronegative substituents to increase the stability of the metal cation-anion pair within the solvated matrix of the polymer in the sensor membrane.

Anions suitable for use in the present invention, include but are not limited to: $ClO_4^-$, $BF_4^-$, $PF_6^-$, $AsF_6^-$, $SbF_6^-$, $(C_6F_5)_4B^-$, $(CF_3CO)_2CH^-$, $CB_{11}H_6Br_6^-$, $CF_3SO_3^-$ and $B(C_6H_5)_4^-$. Common features of these suitable anions include, but are not limited to, low lattice energies for the Ag(I) salts thereof and highly electronegative substituents. The $B(C_6F_5)_4^-$ anion is an example of an anion with aromatic groups in addition to highly electronegative substituents.

In one aspect, the invention is a sensor membrane in the form of a solid solution having a first luminescence emission profile, the solution comprising a luminescent polymer and a metal that binds at least one alkene, preferably a gaseous alkene, the solution having a distinct second luminescence emission profile after exposure to the at least one alkene.

A sensing membrane of the present invention is prepared by dissolving a transition metal salt and a polymer in a liquid solvent to form a coating solution, applying the coating solution to a supporting membrane or surface, and drying the film to produce a solid solution. The liquid solvent used in the process may be any solvent that will dissolve both the polymer and the metal salt, and will allow the facile removal of solvent either by evaporation in the ambient atmosphere or in vacuo. Suitable solvents include but are not limited to: acetonitrile, acetone, tetrahydrofuran, benzene, toluene and other substituted aromatic solvents.

The morphology of the films must be considered and controlled. The thickness should be appropriate for suitable sensing response. The film preferably has a maximum possible ratio of surface area to volume, while maintaining a sufficient level of luminescence. Additionally, films are more effective if they have a uniform morphology and with minimal thickness. The manner in which a film coating solution is applied to a supported membrane can vary, as is already well known. For example dip coating, spin coating, and or other method appropriate to preparation of polymer films may be used. The thickness of the film formed on the supported membrane after drying is preferably as thin as possible to expose the maximum number of sensing sites to the ambient environment for optimal sensing efficiency.

In a preferred aspect, the sensor of the invention is integrated with diode emitters and detectors to make a solid-state electronic device that responds to changes in environmental ethylene concentration.

It is an object of the present invention to sense at least one alkene over a relevant concentration range of between about 10 and about 100,000 ppb, without regard to molecular weight of the alkene(s).

It is an advantage of the present invention that it enables a single system to precisely sense and control alkene level, especially ethylene level. With such an integrated system, alkene levels can be controlled as easily as temperature or humidity. With such technology, one can use a single chamber for both storage and pre-market ripening of freshly harvested fruit.

In addition to enabling and describing the invention over its full scope, it will also be apparent to the skilled person that the accompanying detailed description provides guidance for further optimizing the sensors and methods of the invention.

DETAILED DESCRIPTION OF THE INVENTION

Figure 2:
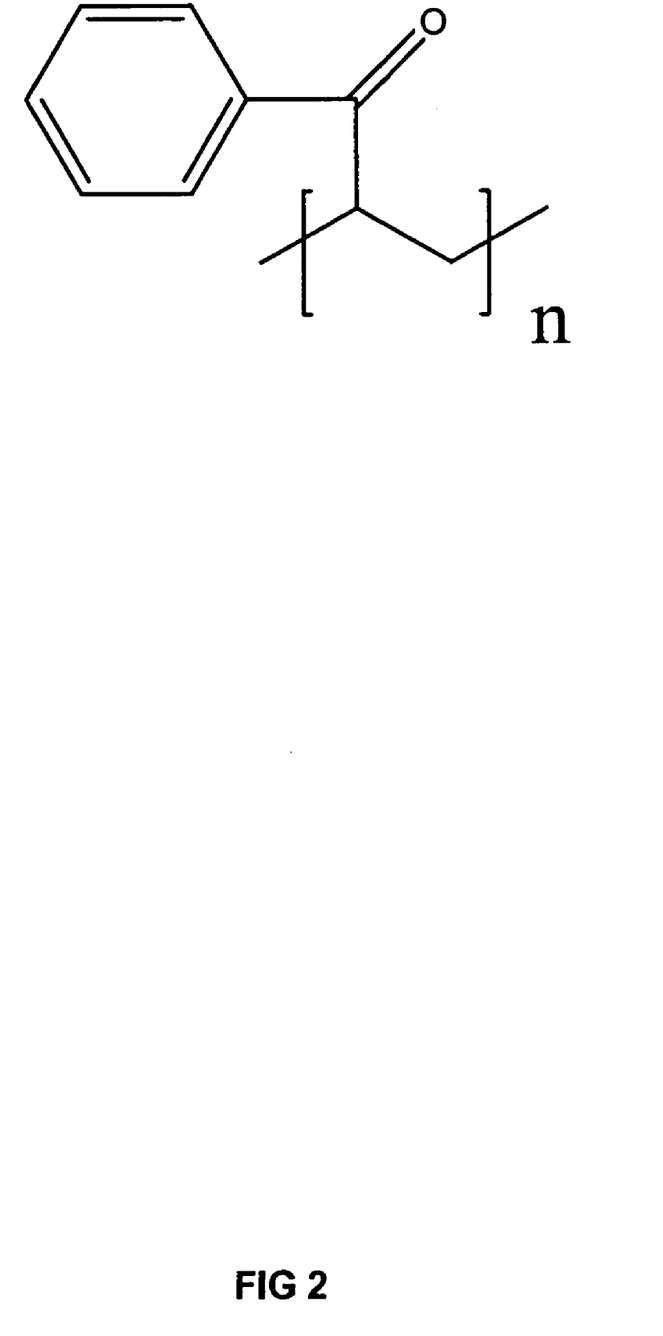
FIG. 2 shows the structure of poly (vinyl phenyl ketone) (PVPK)—the carbonyl and phenyl rings bind to $Ag^+$ ions.

A commercially available, luminescent polymer suitable for use in the invention is poly(vinyl phenyl ketone) (PVPK, FIG. 2). This polymer is closely related to poly(vinyl methyl ketone), a polymer known to promote facilitated transport of alkenes. This inexpensive polymer was employed for proof-of-principle studies.

Figure 3:
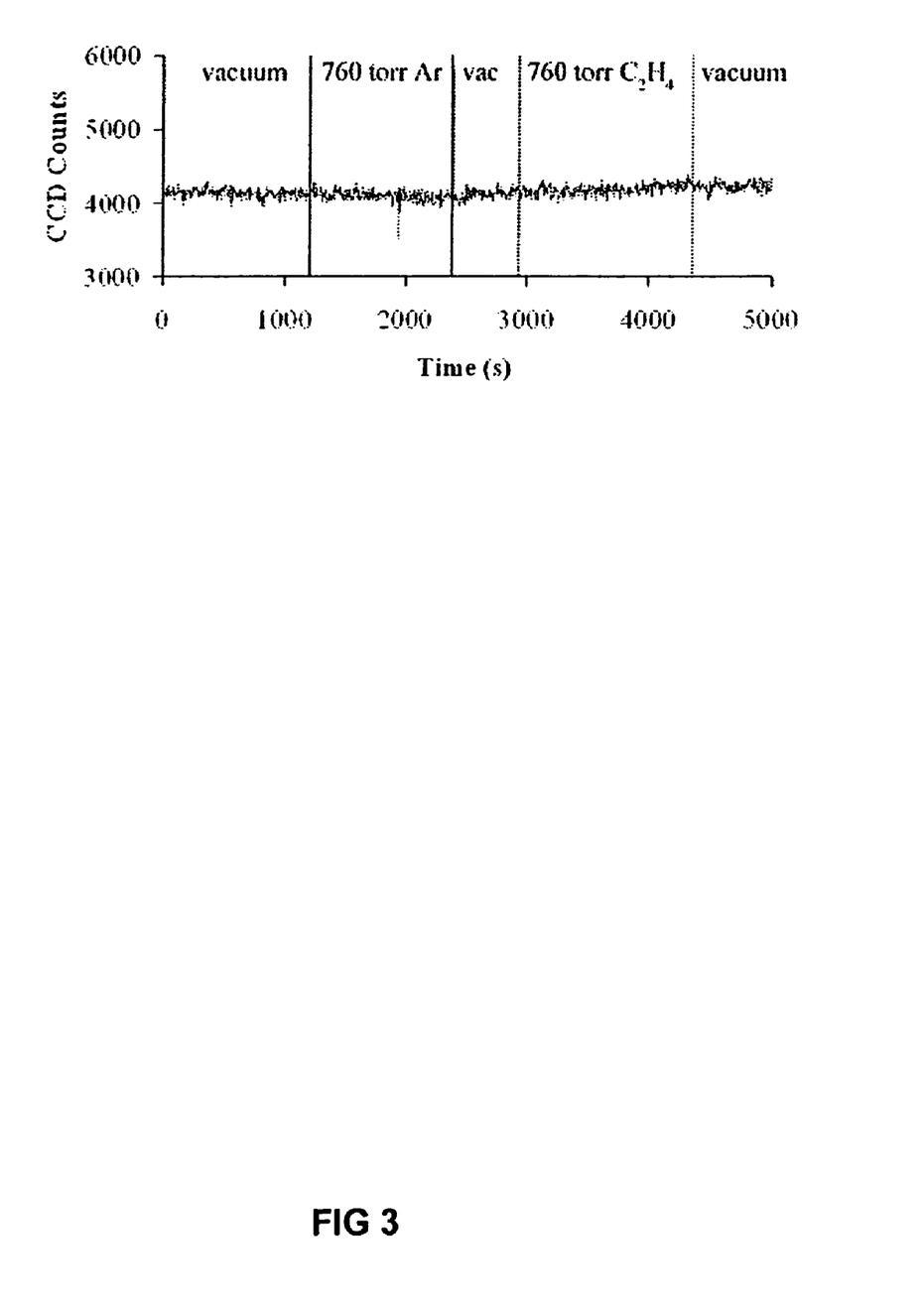
FIG. 3 shows that pure PVPK does not show any luminescence change in response to Ar or ethylene—the plot records the emission intensity at 575 nm in response to atmospheric changes as noted.
Figure 4:
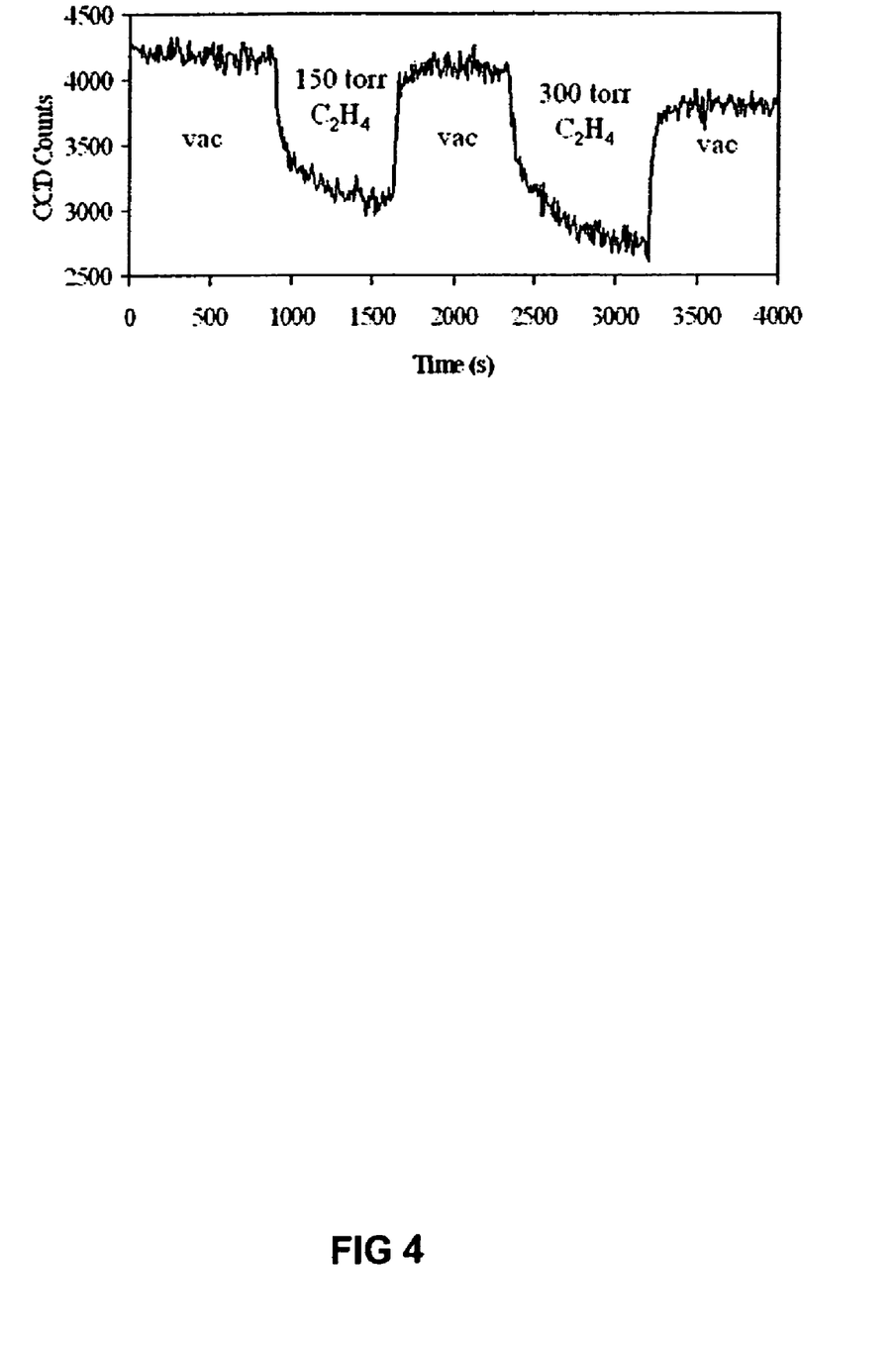
FIG. 4 shows that Ag—impregnated PVPK with 2 mol $Ag^+$ per 1 mol PVPK functional groups (C=O or phenyl) responds reversibly to ethylene.

Initial studies explored the effect of silver doping on PVPK photoluminescence. A PVPK film, prepared on a glass slide by evaporation of an acetonitrile solution of the polymer, exhibited significant luminescence when excited with low intensity laser light (<1 mW). When excited at 488 nm, at the extreme edge of the absorption band, the polymer emitted at 575 nm. This pure PVPK film showed no response to changes in the ambient atmosphere from vacuum to 1 atm Ar or 1 atm ethylene (FIG. 3); the emission intensity and the wavelength of maximum emission remained constant. In subsequent experiments, the emission was monitored at 575 nm for response to changes in the ambient atmosphere of the film.

We prepared potential sensory films by dissolving PVPK and varying concentrations of $AgBF_4$ in acetonitrile, allowing 2 mL of the solution to evaporate from the surface of a glass slide, and drying the film under vacuum inside a luminescence cell designed to allow control of the ambient atmosphere. The $Ag^+$ ion-to-polymer carbonyl group molar ratio was varied from 0.5:1 to 2:1, in order to determine how the polymer response varied with $Ag^+$ content.

Figure 5:
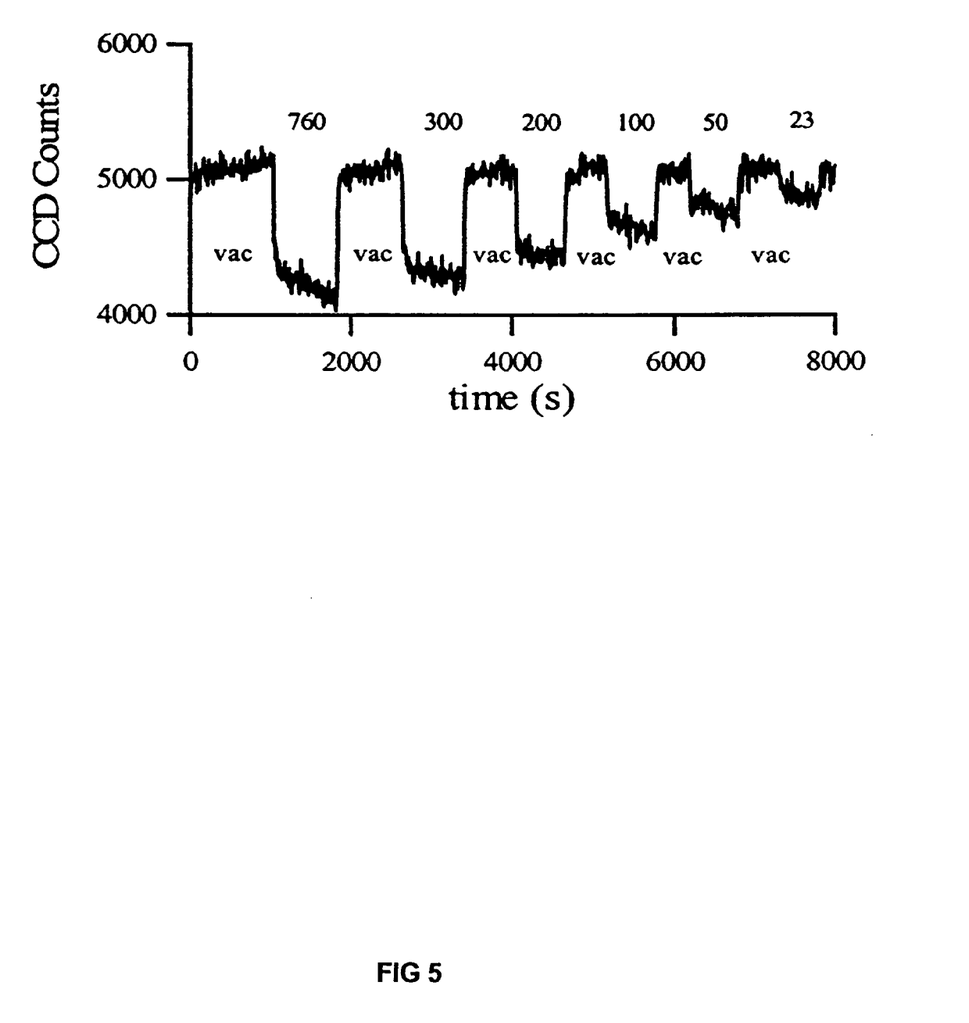
FIG. 5 shows luminescence changes of a conditioned 2:1 $Ag^+$ to PVPK functional groups film exposed to varying concentrations of ethylene—the response is linear up to 300 torr and saturates at higher concentrations.
Figure 6:
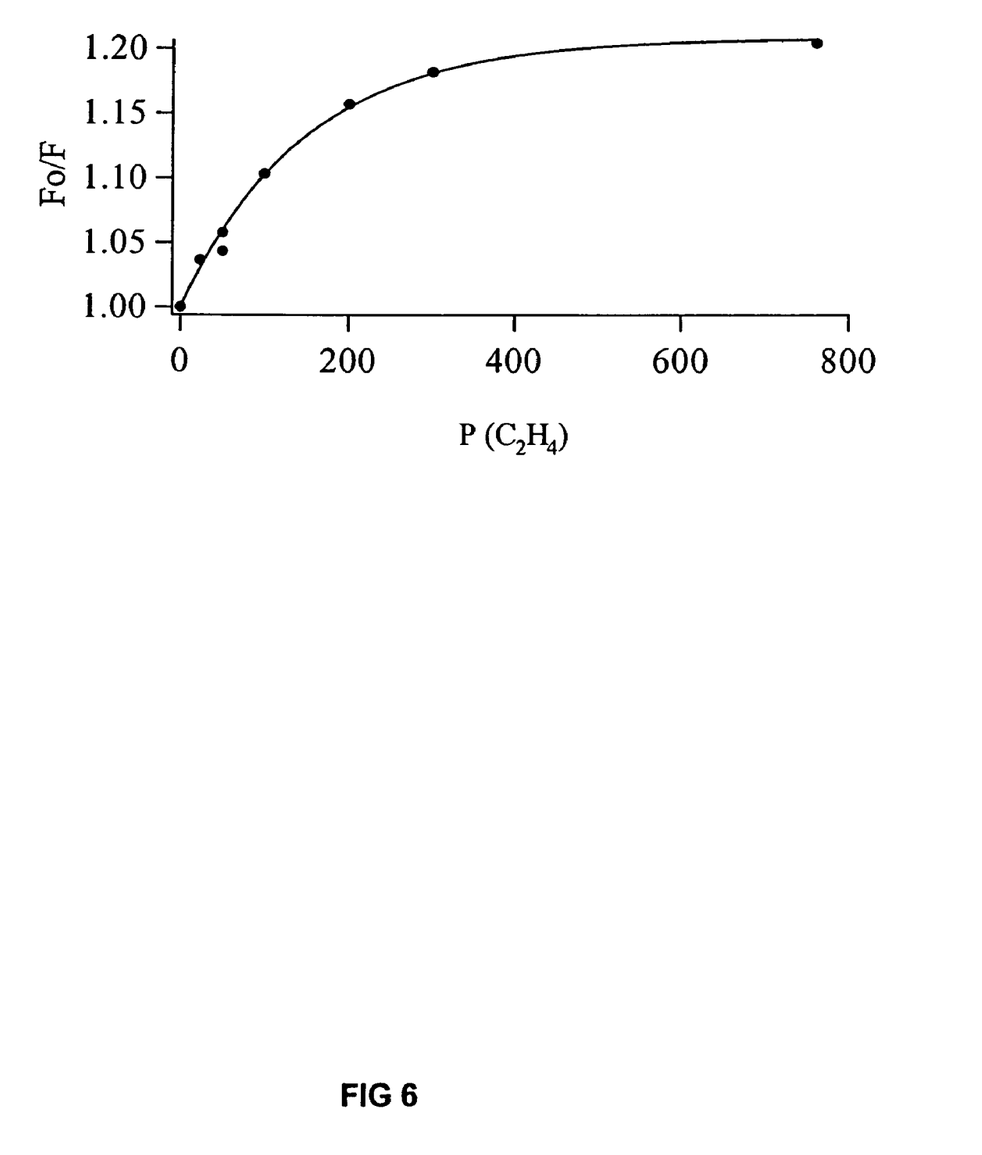
FIG. 6 shows a Stern-Volmer plot of PLo/PL versus ethylene partial pressure for a conditioned 2:1 Ag:PVPK film.

$AgBF_4$-impregnated PVPK responds to ethylene with reversible luminescence quenching, with a magnitude that is proportional to the partial pressure of ethylene. Control films of pure PVPK and PVPK impregnated with $NaBF_4$ show no changes in photoluminescence (PL) upon exposure to ethylene, revealing that the Ag(I) ion is necessary to sensitize the polymer. The nature of the PL response varies with the ratio of $Ag^+$ ions to polymer acetophenone groups, exhibiting a consistent and reversible PL quench at a 2:1 ratio, when all the apparent Ag(I) binding sites (carbonyl and phenyl groups) are saturated. The PL quenching response is proportional to the pressure of ethylene (FIG. 5), and a Stern-Volmer analysis suggests that there are two types of emissive sites in the film, those that are accessible to ethylene and those that are not (FIG. 6). The films are robust and fairly selective, responding similarly to ethylene in the presence of air and water vapor, suggesting that they may be used in the ambient atmosphere. Another gaseous olefin, propylene, also induces a proportional PL change but the response does not saturate.

Figure 8:
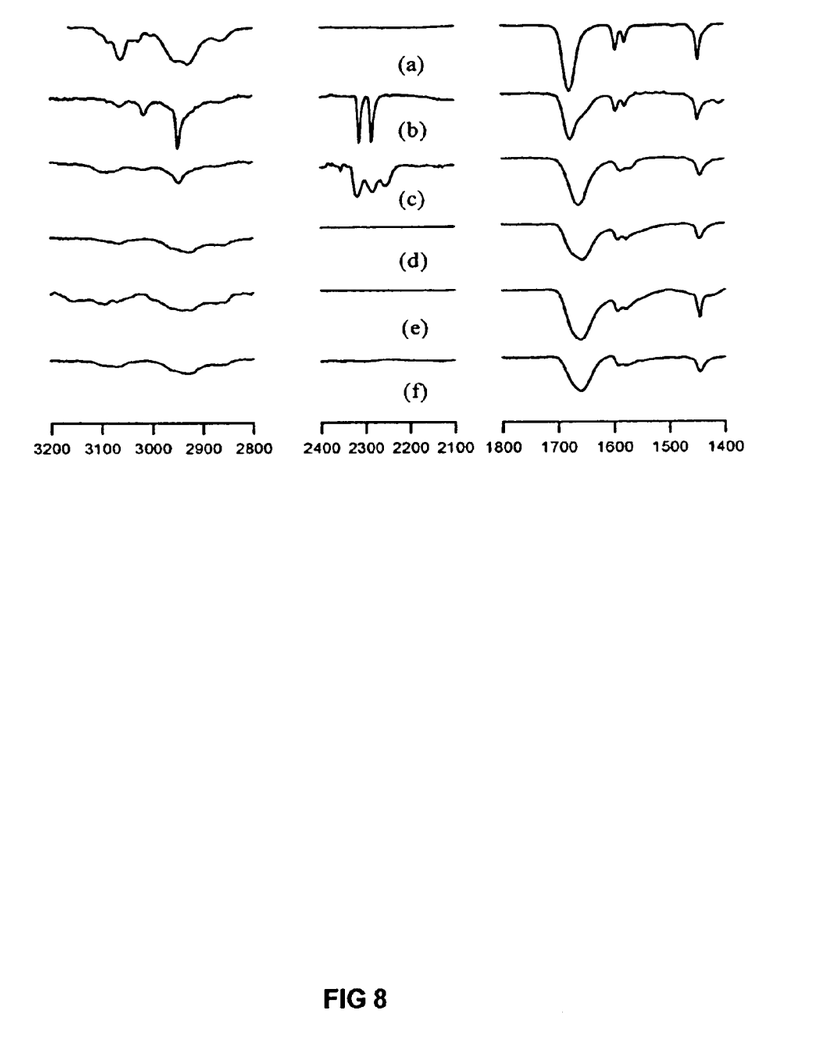
FIG. 8 shows the IR spectra of a CH3CN-cast film during conditioning and sensing: C—H region (left), nitrile region (center) and C=O/C=C region (right). (a) PVPK, (b) 2:1 film as cast, (c) 2:1 film after one conditioning cycle, (d) 2:1 film after six conditioning cycles, (e) 2:1 film after exposure to 1 atm ethylene (under Ar), (f) 2:1 film after exposure to 1 atm ethylene (under vacuum).

The behavior of the Ag-impregnated PVPK films depends on the solvent used to deposit them. Films deposited from $CH_3CN$ solution require an extended conditioning process to remove Ag-coordinated $CH_3CN$. As cast, films contain Ag(I) ions coordinated to solvent molecules (FIG. 8). The conditioning process involves removal of coordinated solvent by alternating exposure to vacuum and 760 torr ethylene; after this process the films respond reversibly to ethylene with PL quenching. THF-cast films require only a single conditioning cycle, rapidly eliminating the THF weakly coordinated to the Ag(I) ions. In contrast, $CH_3CN$-cast films require 6 cycles of conditioning over 6 hours to remove Ag(I)-coordinated $CH_3CN$.

The 2:1 $Ag^+$:carbonyl PVPK films, without significant optimization, are sensitive to 180 ppm ethylene, close to the 100 ppm level used to ripen tomatoes and bananas. Technology already exists for use of luminescent sensory films in solid state devices for gas sensing, and the sensory films developed through this project are well suited to incorporation into these devices.

Further systematic enhancements to the sensors of the invention are specifically contemplated below, particularly with regard to 1) increasing the response sensitivity and 2) shifting the excitation wavelengths into the range accessible by commercially available LEDs to facilitate device construction.

A. Optimization of Polymer Electronic Attributes

Although PVPK can function as a luminescent ethylene sensor, the polymer has limitations as a practical commercial sensor matrix. For example, upon exposure to 366 nm light, PVPK is susceptible to photodegradation through a n->π*-induced Norrish type II photoelimination process. To prevent photodegradation, we excite into the tail of the absorption envelope, at 488 nm, thereby significantly reducing the quantum yield and limiting the luminescence output of the film. Furthermore, 488 nm light is not accessible using inexpensive LED devices, limiting the potential applicability of PVPK in a commercially viable sensor device.

Figure 7:
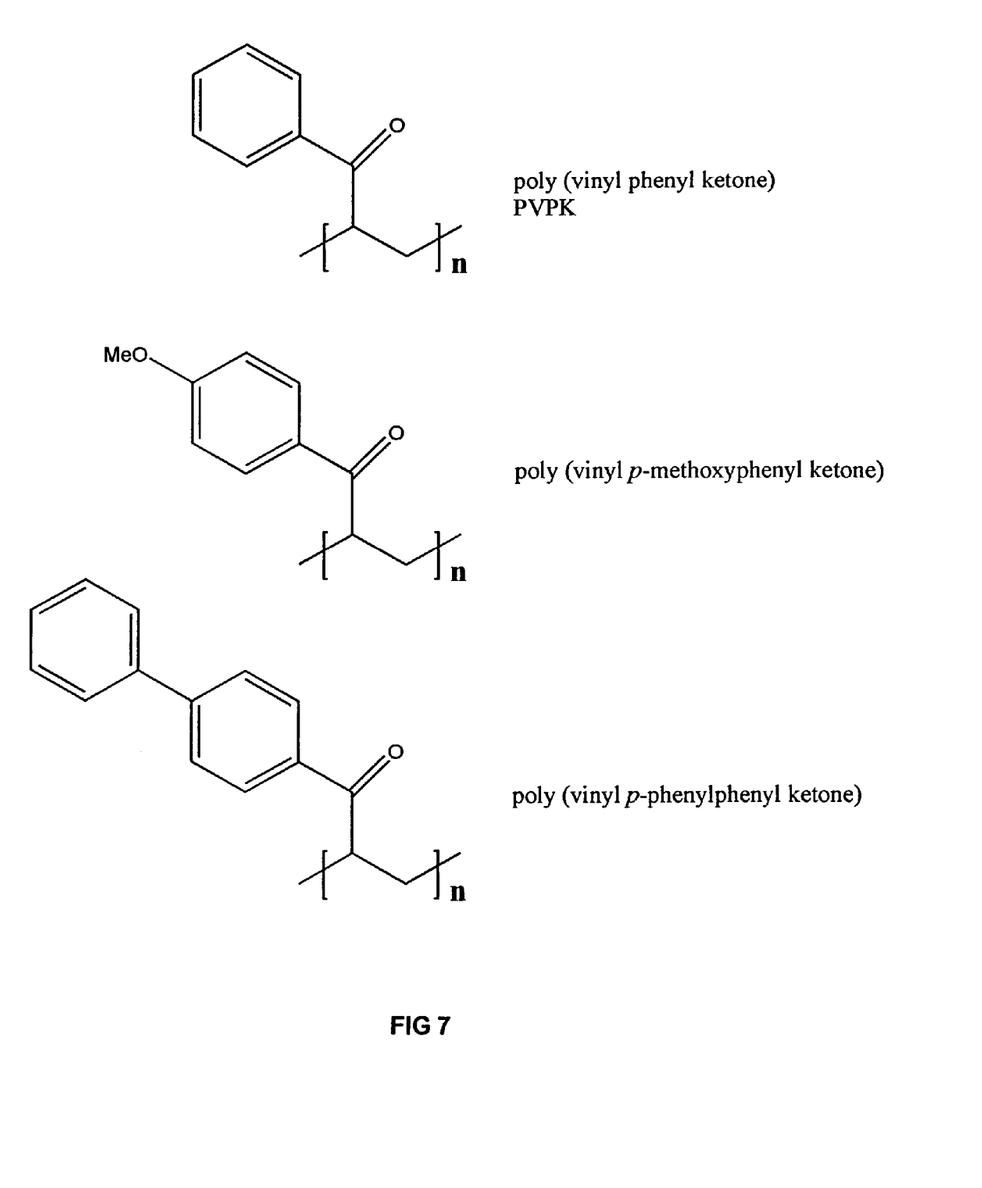
FIG. 7 shows the structure of PVPK and other polymers suitable for use in the invention.

The excitation and emission properties of the polymer can be improved by modifying the polymer structure. Two types of backbone modification are specifically contemplated: 1) electron donating groups can be added to the phenyl rings, and 2) the conjugation can be extended by replacing the phenyl rings with larger aromatic substituents. Both modifications shift the absorption maximum to lower energy and also cause the lowest energy excitation to occur into a non-photodegradative $\pi \to \pi^*$ transition. The skilled artisan can readily vary the monomer and the polymerization procedure, using literature-available methods, to produce new polymers having improved optical properties. The structures of several polymers, including PVPK, suitable for use in the invention are shown in FIG. 7.

Each new polymer can be characterized and assessed for sensor activity in photoluminescence experiments. The polydispersity of the synthesized polymers can be determined by gel permeation chromatography. New polymers can also be characterized by vibrational spectroscopy (IR and Raman) to determine the frequencies of the aliphatic and aromatic C—H modes, the carbonyl modes and the phenyl ring modes. These characteristic vibrations can be used to monitor the interaction of the polymer functional groups with metal ions and with ethylene. Films of the polymer can be prepared using processing procedures optimized for PVPK, as described below, both with and without impregnated metal salts. The emission properties of the films, including the excitation and emission profiles, the quantum yield, and the power dependence, can be determined. The ethylene response of the novel polymer films bearing varying amounts of metal ions can be measured by monitoring the luminescence output of the film as a function of ethylene concentration.

Polymers with desirable emission characteristics and ethylene response can also be used in the experiments described herein, to optimize the response through modulation of the metal salt and the processing strategy. At each stage, effective sensory materials can be selected for further development and characterization.

B. Optimization of Metal Salt Properties for Ethylene Binding

By varying the identity of the counter-ion, one can vary the ability of the metal center to interact with ethylene. Polymer films can be prepared in the presence of varying concentrations of silver salts, in which the counter-anion is larger or more massive than $BF_4^-$. In general, one can use highly fluorinated counter-anions to minimize the interaction of the anion with the $Ag^+$ ion. Suitable counter-ions that can be used in these experiments include $PF_6^-$, $SbF_6^-$, $B(C_6F_5)_4^-$, $B(C_6H_5)_4^{-31}$ and $CF_3SO_3^-$. Larger counter-ions increase sensitivity to ethylene, but also result is films that are less stable to photodegradation.

The emission properties of films prepared with each counter-anion can be determined, and the response of the films to varying concentrations of ethylene can be measured. When appropriate, ethylene-binding data can be analyzed using the Stern-Volmer model and binding constants can be calculated. The stability of the sensing films can be determined by monitoring the baseline emission and the response to ethylene over time.

Because Ag(I) ion may be susceptible to photoreduction, the stability of the film under continuous irradiation at varying intensity can also be determined. Stable films giving rise to high binding constants and large luminescence changes can be obtained and characterized.

Since the metal ion-ethylene interaction is the primary force governing ethylene binding within the matrix, another way to increase ethylene-binding activity is to change the identity of the metal ion. Copper(I) is calculated to form a bond to ethylene that is 50% stronger than the bond between silver(I) and ethylene; therefore, replacing $Ag^+$ with $Cu^+$ is expected to increase the sensitivity of the film. One can explore the chemistry of films prepared from a variety of copper salts; the Cu(I)-containing starting materials will be the acetonitrile-stabilized $[Cu(CH_3CN)_4]X$ salts, where X is any of the anions mentioned above. Polymer films containing varying concentrations of copper salts can be prepared under rigorously anaerobic conditions in a dry box, and can be sealed inside the luminescence cell under inert atmosphere. The films can be characterized using the methods described for the silver salt-containing films.

To determine whether the $Cu^+$ ion is stable within the polymer matrix, the response of these copper-containing films can be monitored over time, both for stability of the emission intensity and the responsiveness to ethylene. Because buildup of paramagnetic $Cu^{2+}$ ion in the polymer would be expected to lead to quenching of the emission, the luminescence of such films can be monitored in the absence of ethylene and $Cu^{2+}$ content can be determined by EPR spectroscopy. If copper-containing films prove to be more sensitive to ethylene and are adequately stable for possible use in sensing devices, the films can be further characterized.

One can evaluate the selectivity of the films with the highest ethylene binding constants and largest luminescence changes generated from the silver or copper salts to identify additional film candidates for use in an ethylene sensor device. Since a sensor that can operate in the open air is most desirable, it is important to assess the response of the sensor films to the major ($O_2$, $N_2$) and minor (Ar, $CO_2$) components of air and the responses to these and other components, such as CO, can be measured. The most likely interference among these gases is with $O_2$, especially in the case of $Cu^+$ ion. Films containing $Cu^+$ ion may also respond to CO, and since perishable plant products may be exposed to CO during transport, interference from CO is undesirable. A preferred ethylene sensor will substantially respond only to ethylene, with only minimal response to any other gas. A film showing the best combination of substantially complete response to ethylene with minimal response to other gases can be selected for possible device development. If interference from another gas cannot be eliminated, a scrubber prior to the sensor can be included in a final fabricated device.

C. Surface Optimization

Film processing methods provide another means to improve the response to ethylene in metal-impregnated polymers. Promising ethylene sensing results with the 2:1 Ag:carbonyl PVPK polymer were obtained with crudely prepared films, and microscopic examination of those films revealed highly irregular surfaces (vide supra). Numerous strategies have been developed for producing uniform, high surface-to-volume ratio films of polymeric materials on a variety of substrates. Effective methods include chemical modification of the substrate and specialized film deposition processes. Uniform monolayers are expected to maximize the percentage of metal centers capable of reversibly binding ethylene, generating a maximal response with a minimal amount of material. Glass slides cleaned with an ethanolic solution of NaOH can be effectively wetted with a single drop of PVPK/$Ag^+$ in $CH_3CN$, ⅒ the volume to prepare the functional sensing film on untreated slides.

Additional strategies can be employed to produce high surface area monolayers to prepare polymer films for all sensing applications. Initially, one can optimize the surface processing for the 2:1 Ag: carbonyl PVPK film, and any other films employed in accord with the invention, to optimize response while minimizing the amount of material employed. One can also chemically modify the glass substrate to maximize the surface wetting by the acetonitrile-solvated polymer and metal salt. Suitable strategies can include pretreatment of the glass surface with acid or base, and covalent modification with silanizing reagents. Additionally, the films can be prepared by drop spreading, dip coating, spin coating and Langmuir-Blodgett methods, any of which may be particularly well suited to performance of a given film. Preferably suitable processing conditions can be identified for a film of interest such that reversible, concentration dependent responses to ethylene without a need to precondition the film.

Imprinting is another strategy to improve film responsiveness to ethylene. Ethylene responsiveness depends on the interaction of the ethylene molecule with metal cations within the heterogeneous polymer matrix. The metal ion is also bound to the polymer functional groups and to the counter-anion, and the ethylene molecule must effectively compete with these other interacting groups. A polymer matrix prepared in the presence of ethylene is expected to contain metal ions that are already bound to ethylene, with optimal counter-anion and polymer functional group interactions established. When ethylene is subsequently removed, optimized ethylene binding sites should remain within the film. Imprinted films can be prepared from ethylene-saturated solutions and dried under a flow of ethylene. Once the film is dry, the bound ethylene can be removed by heating the polymer film under vacuum. Films prepared in this manner can be tested for luminescence response to varying ethylene concentrations.

D. Spectroscopic Characterization of Sensing Events

Films that prove highly responsive and selective for ethylene binding can be subjected to spectroscopic study in order to elucidate the chemistry of the sensing event. Vibrational spectroscopy is an exceptionally valuable tool for studying these interactions, as the polymer, counter-anion, and analyte exhibit characteristic vibrational frequencies. Coordination to a metal ion alters the vibrational frequencies of bonds containing the donor atom; therefore, one can determine which functional groups are interacting directly with the metal cations. Using IR and/or Raman spectroscopy, one can determine which functional groups bind the metal cation and how these interactions change upon ethylene binding. The specific vibrational modes that can be monitored can include the aromatic rings and carbonyl groups of the polymer, the vibrations of the counter-anion (generally X-F modes), and the C-D and C=C modes of bound $C_2D_4$. Isotopic labeling of ethylene permits differentiation of the vibrations of the bound ligand from those of the polymer. The glass substrate used in the photoluminescence experiments is Raman inactive, and thus identical films may be used in both luminescence and Raman experiments. Fluorescence, which is a potential interference in luminescent polymers, can be minimized by an appropriate choice of Raman excitation wavelength. Films for IR spectroscopy must be prepared on matrices compatible with the method, such as Teflon membranes or salt plates. Prior to IR experiments, films prepared on IR-compatible substrates can be tested in the photoluminescence experiment to ensure that the films respond appropriately to ethylene. If greater sensitivity is needed to study thin polymer films, surface enhanced Raman scattering (SERS) on silver or gold surfaces or total internal reflectance IR on appropriate substrates can be used.

We characterized the molecular changes that occur during film deposition, conditioning and sensing in a 2:1 Ag:carbonyl PVPK film. FIG. 8 shows IR spectroscopic monitoring of the response of a 2:1 Ag:carbonyl PVPK film to successive changes in ambient atmosphere. In a freshly prepared film, a limited shift of the carbonyl resonance is observed, suggesting that the $Ag^+$ ions interact to a limited extent with the polymer carbonyl groups. Conditioning the polymer by alternating exposure to ethylene and vacuum washes out residual acetonitrile solvent bound to the $Ag^+$ ions, resulting in loss of the cyanide stretch (b, c, d). Selection of an alternate solvent, such as tetrahydrofuran, can eliminate the need for extended conditioning. In the conditioned polymer, shown in spectrum d), the silver ions interact with the carbonyl groups as evidenced by the substantial shift in the carbonyl frequency. When this film is re-exposed to ethylene, only minor changes are observed, suggesting that the polymer carbonyls remain coordinated to $Ag^+$. Changes in the peak width of the aryl C=C stretch suggest that the polymer phenyl rings may coordinate to the $Ag^+$ and that ethylene binding may displace the phenyl rings from the metal. A plausible explanation for the luminescence quench observed in response to ethylene is that simultaneous coordination of ethylene and the polymer carbonyl groups provides a pathway for non-emissive vibrational relaxation of the excited polymer.

The present invention is not intended to be limited to the foregoing, but rather to embrace all such modifications and variations as fall within the scope of the appended claims.

We claim:

1. A solid solution having a first photoluminescence emission profile, the solution comprising:
   a transition metal capable of binding at least one alkene; and
   a photoluminescent polymer having an extended conjugated moiety coordinately covalently bound to a transition metal,
   wherein the solution has a distinct second photoluminescence emission profile upon coordinated interaction among the polymer, the transition metal and the at least one alkene.

2. The solid solution of claim 1, wherein the polymer is poly(vinyl phenyl ketone).

3. The solid solution of claim 1, wherein the transition metal is Ag(I).

4. The solid solution of claim 1, wherein the alkene is a gaseous alkene.

5. The solid solution of claim 1, wherein the alkene is ethylene.

6. The solid solution of 2, wherein the alkene is ethylene.

7. A solid solution as claimed in claim 1 wherein the polymer is photoluminescent upon exposure of the solution to light at an emission-inducing wavelength.

8. A solid solution as claimed in claim 1 wherein the polymer is selected from the group consisting of poly(vinyl phenyl ketone), poly(vinyl p-methoxyphenyl ketone) and poly(vinyl p-phenylphenyl ketone).

9. A sensor for sensing at least one alkene, the sensor comprising:
   a solid solution having a first photoluminescence emission profile,
   an irradiation source capable of directing photoluminescent emission by the solid solution; and
   a detector for measuring photoluminescent emission by the solid solution,
   wherein the solution comprises a transition metal capable of binding the at least one alkene and a photoluminescent polymer having an extended conjugated moiety, the metal and the conjugated moiety being electronically coordinated and forming a sensing locus, the solution having a distinct second photoluminescence emission profile upon electronic interaction between the sensing locus and the at least one alkene.

10. The sensor of claim 9 wherein at least one of the irradiation source and the detector is integrally formed with the solid solution.

11. The sensor of claim 9, wherein the polymer is poly(vinyl phenyl ketone).

12. The sensor of claim 9, wherein the transition metal is Ag(I).

13. The sensor of claim 9, wherein the alkene is a gaseous alkene.

14. A sensor as claimed in claim 9 wherein the polymer is photoluminescent upon exposure of the solution to light at an emission-inducing wavelength.

15. A method of sensing an alkene, the method comprising:

providing a sensor in an environment that may contain at least one alkene, the sensor comprising a solid solution having a first photoluminescence emission profile, an irradiation source capable of directing photoluminescent emission by the solid solution, and a detector for measuring photoluminescent emission by the solid solution, the solid solution comprising a transition metal capable of binding the at least one alkene and a photoluminescent polymer having an extended conjugated moiety, the metal and the conjugated moiety being electronically coordinated and forming a sensing locus, the solution having a second photoluminescence emission profile upon electronic interaction between the sensing locus and the alkene;

exposing the sensor to light at an emission-inducing wavelength in the presence of the at least one alkene; and observing a photoluminescence emission profile characteristic of the electronic interaction between the sensing locus and the at least one alkene.

16. A method of sensing an alkene as claimed in claim 15 wherein the polymer is poly(vinyl phenyl ketone).

17. A method of sensing an alkene as claimed in claim 15 wherein the transition metal is Ag(I).

18. A method of sensing an alkene as claimed in claim 15 wherein the alkene is a gaseous alkene.

19. A method of sensing an alkene as claimed in claim 15 wherein the alkene is ethylene.

20. A method as claimed in claim 15 further comprising the step of exposing the sensor to light at an emission-inducing wavelength, wherein the polymer is photoluminescent upon exposure of the solution to light at the emission-inducing wavelength.

* * * * *